(12) United States Patent
Roesky et al.

(10) Patent No.: US 8,598,284 B2
(45) Date of Patent: Dec. 3, 2013

(54) OXYGEN-BRIDGED BIMETALLIC COMPLEX AND POLYMERIZATION PROCESS

(75) Inventors: Herbert W Roesky, Gottingen (DE); Prabhuodeyara M Gurubasavaraj, Nara (JP)

(73) Assignee: Georg-August-Universitat Goettingen, Gottingen (DE)

( * ) Notice: Subject to any disclaimer, the term of this patent is extended or adjusted under 35 U.S.C. 154(b) by 566 days.

(21) Appl. No.: 12/879,088

(22) Filed: Sep. 10, 2010

(65) Prior Publication Data
US 2011/0015356 A1  Jan. 20, 2011

Related U.S. Application Data

(62) Division of application No. 12/110,738, filed on Apr. 28, 2008, now Pat. No. 7,888,522.

(60) Provisional application No. 60/914,170, filed on Apr. 26, 2007.

(51) Int. Cl.
*C08F 4/76* (2006.01)
*C08F 4/64* (2006.01)
*C08F 4/52* (2006.01)

(52) U.S. Cl.
USPC ............ 526/116; 526/113; 526/114; 526/348

(58) Field of Classification Search
USPC .................... 526/348, 113, 116, 114
See application file for complete search history.

(56) References Cited

U.S. PATENT DOCUMENTS 5,051,481 A * 9/1991 Taka et al. ............ 525/240
5,354,842 A * 10/1994 Kamiya et al. ............ 528/503

| 5,688,733 A | 11/1997 | Renkema et al. |
| 6,426,395 B1 | 7/2002 | Yamazaki et al. |
| 6,528,448 B1 | 3/2003 | Jensen et al. |

FOREIGN PATENT DOCUMENTS

| WO | WO0183498 | 11/2001 |
| WO | WO2004060864 | 8/2004 |
| WO | WO2005044866 | 5/2005 |
| WO | WO2005090373 | 9/2005 |
| WO | WO2006065001 | 6/2006 |

OTHER PUBLICATIONS

Bai et al., "Mononuclear aluminum hydroxide for the design of well-defined homogeneous catalysts," *J. Am. Chem. Soc.*, 2005, 127:3449-3455.
Britovsek et al., "The search for new-generation olefin polymerization catalysts: life beyond metallocenes," *Angew. Chem. Int. Ed. Engl.*, 1999, 38:428-447.

(Continued)

*Primary Examiner* — Rip A. Lee
(74) *Attorney, Agent, or Firm* — Fish & Richardson P.C.

(57) ABSTRACT

An oxygen-bridged bimetallic complex of the general formula (I)

$$Cp_2R^1M^1\text{-}O\text{-}M^2R^2{}_2Cp \qquad (I),$$

wherein

Cp is independently a cyclopentadienyl, indenyl or fluorenyl ligand which can be substituted, or a ligand isolobal to cyclopentadienyl, $R^1$, $R^2$ independently are halide, linear or branched or cyclic alkyl, aryl, amido, phosphido, alkoxy or aryloxy groups, which can be substituted, $M^1$ is Zr, Ti or Hf, and $M^2$ is Ti, Zn, Zr or a rare earth metal.

The complex can be useful as a polymerization catalyst.

7 Claims, 6 Drawing Sheets

(56) References Cited

OTHER PUBLICATIONS

Ditchfield et al., "Self-consistent molecular-orbital methods. IX. An extended Gaussian-type basis for molecular-orbital studies of organic molecules," *J. Chem. Phys.*, 1971, 54:724-728.

Foster and Weinhold, "Natural hybrid orbitals," *J. Am. Chem. Soc.*, 1980, 102:7211-7218.

Gurubasavaraj et al., "Oxygen effect in heterobimetallic catalysis: the Zr—O—Ti system as an excellent example for olefin polymerization," *Organometallics*, 2007, 26 (14): 3346-3351.

Gurubasavaraj et al., "Synthesis, structural characterization, catalytic properties, and theoretical study of compounds containing an Al—O—M (M = Ti, Hf) core," *Inorg. Chem.*, 2007, 46(4):1056-61.

Hariharan and Pople, "The influence of polarization functions on molecular orbital hydrogenation energies" *Theoretica Chimica Acta*, 1973, 28(3): 213-222.

Hay and Wadt, "*Ab initio* effective core potentials for molecular calculations. Potentials for the transition metal atoms Sc to Hg," *J. Chem. Phys.*, 1985, 82:270-283.

Ishino et al., "Olefin polymerization catalyzed by titanium—tungsten heterobimetallic dinitrogen complexes," *Organometallics*, 2004, 23(20): 4544-4546.

Kreuder et al., "Early metal carborane chemistry. Generation and reactivity of (C5Me5)(.eta.5-C2B9H11)TiMe" *Organometallics*, 1995, 14 (6): 2993-3001.

Lee et al., "Development of the Colle-Salvetti correlation-energy formula into a functional of the electron density," *Phys. Rev. B*, 1988, 37(2): 785-789.

Manriquez et al., "Reduction of carbon monoxide promoted by alkyl and hydride derivatives of permethylzirconocene," *J. Am. Chem. Soc.*, 1978, 100(9): 2716-2724.

Manriquez et al., "Solution structure and dynamics of binuclear dinitrogen complexes of bis(pentamethylcyclopentadienyl)titanium(II) and bis(pentamethylcyclopentadienyl)zirconium(II)," *J. Am. Chem. Soc.*, 1978, 100(10): 3078-3083.

Mena et al., "Electron-deficient (pentamethylcyclopentadienyl)titanium trialkyls: evidence of Ti•••H—C and Ti•••C—C interactions. Crystal and molecular structure of $\mu$-[$o$-(CH$_2$)$_2$C$_6$H$_4$]{($\eta^5$-C$_5$Me$_5$)Ti[$o$-(CH$_2$)$_2$C$_6$H$_4$]}$_2$," *Organometallics*, 1989, 8:476-482.

Miehlich et al., "Results obtained with the correlation energy density functionals of Becke and Lee, Yang and Parr," *Chem. Phys. Lett.*, 1989. 157:200-206.

Rassolov et al., "6-31G basis set for third-row atoms," *J. Comp. Chem.*, 2001, 22:976-984.

Reed and Weinhold, "Natural localized molecular orbitals," *J. Chem. Phys.*, 1985, 83(4):1736-1740.

Reed et al., "Intermolecular interactions from a natural bond orbital, donor-acceptor viewpoint," *Chem. Rev.*, 1988, 88 (6):899-926.

Sheldrick, "Phase annealing in SHELX-90: direct methods for larger structures," *Acta Cryst.* (1990). A46, 467-473.

Singh and Roesky, "Robust and efficient molecular catalysts with a M-O-M' framework," *Dalton Trans.*, 2007, 1360-1370, DOI: 10.1039/B614558B, published online Mar. 7, 2007.

\* cited by examiner

PE = polyethylene

OXYGEN-BRIDGED BIMETALLIC COMPLEX AND POLYMERIZATION PROCESS

CROSS-REFERENCE TO RELATED APPLICATIONS

This application is a divisional of U.S. application Ser. No. 12/110,738, filed Apr. 28, 2008, now U.S. Pat. No. 7,888,522, which claims priority from U.S. Provisional Application Ser. No. 60/914,170, filed Apr. 26, 2007.

BACKGROUND

In recent years there has been immense interest in preparing catalysts to produce linear low density polyethylene (LL-DPE). Compared to conventional polymers of ethylene, LLDPE offers the following rheological and mechanical properties: high tensile strength, higher impact and puncture resistance, superior toughness, good organoleptics and low blocking, excellent clarity and gloss, and easy blends with other polyolefins. LLDPE can be obtained from the polymerization of ethylene by using Ziegler-Natta catalysts (zLL-DPE) or by metallocene catalysts (mLLDPE), which are formed by the reaction of group 4 metallocene with a coactivator, of which methylalum(in)oxane (MAO) is most typical. In the case of conventional Ziegler-Natta catalysts, zLLDPE suffers in terms of clarity or stiffness, but by using metallocene catalysis, some long chain branching is introduced, which improves clarity, whereas mLLDPE is difficult to process into films. Incorporation of a small level of branching into the LLDPE leads to excellent processibility and high melt tensions suitable for film manufacture. Typically, LLDPE branching is achieved via copolymerization of ethylene with a linear α-olefin comonomer. LLDPE can also be obtained by single site constrained-geometry catalysts (CGCs), which are based on cooperative effects between active centers in multinuclear complexes.

SUMMARY

This document provides oxygen-bridged bimetallic complexes that can be used as catalysts for the olefin polymerization. The catalysts employed can lead to an advantageous match of mechanical and chemical properties of the obtained polyolefins, e.g., a desired degree of branching in polyethylene.

The object is achieved by an oxygen-bridged bimetallic complex of the general formula (I)

  (I)

wherein
Cp is independently a cyclopentadienyl, indenyl or fluorenyl ligand which can be substituted, or a ligand isolobal to cyclopentadienyl;
$R^1$, $R^2$ independently are halide, linear or branched or cyclic alkyl, aryl, amido, phosphido, alkoxy or aryloxy groups, which can be substituted,
$M^1$ is Zr, Ti or Hf,
$M^2$ is Ti, Zn, Zr or a rare earth metal.

According to the present document, a facile route for the preparation and catalytic property of a Ti—O—Zr containing compound by the reaction of a tailor made precursor such as $Cp*_2ZrMe(OH)$ ($Cp*=C_5Me_5$) and the titanium component has been identified. The heterobimetallic complex exhibits greater activity towards olefin polymerization and produces LLDPE with small but significant levels of $C_4$-$C_6$ alkyl branching in comparison with its mononuclear precursor mixture A ($Cp*_2ZrMe_2$ and $Cp*TiMe_3$), which gives LLDPE under the same condition with negligible branching.

In the oxygen-bridged bimetallic complex of the general formula (I) Cp can be independently (i.e., each position in the complex can have one of the following meanings independent of the meanings of the other Cp-ligands) a cyclopentadienyl, indenyl or fluorenyl ligand or a ligand isolobal to cyclopentadienyl. The ligands can be substituted or unsubstituted. Possible substituents are aliphatic groups, cyclic groups, a combination of aliphatic groups and cyclic groups, silyl groups, alkyl halide groups, halides, organometallic groups, phosphorous groups, nitrogen groups, silicon, phosphorus, boron, or germanium. Aliphatic groups can be, for example, $C_{1-12}$-alkyl groups (e.g., $C_{1-6}$-alkyl groups or $C_{1-3}$-alkyl groups, such as methyl, ethyl, propyl or iso-propyl groups). One or more of the carbon atoms forming the cyclopentadienyl, indenyl or fluoroenyl ligand can be substituted in this manner. Other substituents such as $SiR_3$, $SnR_3$, $PR_2$, $NR_2$ wherein each R independently is alkyl, aryl, halide or pseudohalide, as defined above, also can be present. In some embodiments, each Cp independently is a cyclopentadienyl ligand which can be substituted by 1 to 5 $C_{1-6}$-alkyl groups (e.g., by 5 $C_{1-3}$-alkyl groups). For example, each Cp* ligand can be pentamethylcyclopentadienyl. In another example, all three Cp ligands in formula (I) can be Cp*.

$R^1$, $R^2$ independently can be halide, linear or branched or cyclic alkyl, aryl, amido, phosphido, alkoxy or aryloxy groups, which can be substituted. The substituents can be the same as the substituents listed above for Cp. By way of example and not limitation, alkyl groups can be $C_{1-12}$-alkyl groups (e.g., $C_{1-6}$-alkyl groups), branched alkyl groups can be $C_{3-12}$-alkyl groups (e.g., $C_{3-6}$-alkyl groups), cyclic alkyl groups can be $C_{5-7}$-cycloalkyl groups (e.g., cyclohexyl groups), aryl groups can be phenyl groups, and possible substituents can be $C_{1-6}$-alkyl groups. $R^1$ and $R^2$ independently can be $C_{1-6}$-alkyl groups (e.g., $C_{1-3}$-alkyl groups, such as methyl groups).

In some embodiments, the complex of the general formula (I) can be $Cp*_2MeZr$—O—$TiMe_2Cp*$.

This document also relates to a process for preparing the complex of the general formula (I) by reacting a complex of the general formula (II)

  (II)

with a complex of the general formula (III)

  (III)

wherein Cp, $R^1$, $R^2$, $M^1$ and $M^2$ have the meanings defined above.

Specific reaction conditions are exemplified below.

This document also relates to a complex of the general formula (II)

  (II)

wherein
Cp is independently a cyclopentadienyl, indenyl or fluorenyl ligand which can be substituted, or a ligand isolobal to cyclopentadienyl.
$M^1$ is Zr, and
$R^1$ is a halide, linear or branched or cyclic alkyl, aryl, amido, phosphido, alkoxy or aryloxy group that can be substituted.

In some embodiments, the complex of the formula (II) can be Cp*ZrMe(OH).

Thus, in one aspect, this document features an oxygen-bridged bimetallic complex of the general formula (I)

$$Cp_2R^1M^1\text{-}O\text{-}M^2R^2_2Cp \qquad (I)$$

wherein

Cp is independently a cyclopentadienyl, indenyl or fluorenyl ligand which can be substituted, or a ligand isolobal to cyclopentadienyl, $R^1$ and $R^2$ independently are halide, linear or branched or cyclic alkyl, aryl, amido, phosphido, alkoxy or aryloxy groups, which can be substituted, $M^1$ is Zr, Ti or Hf, and $M^2$ is Ti, Zn, Zr or a rare earth metal.

For example, Cp independently can be a cyclopentadienyl ligand that can be substituted by 1 to 5 $C_{1\text{-}6}$-alkyl groups, $R^1$ and $R^2$ independently can be $C_{1\text{-}6}$-alkyl groups, $M^1$ can be Zr, and/or $M^2$ can be Ti.

In another aspect, this document features a process for preparing an oxygen-bridged bimetallic complex of the general formula (I)

$$Cp_2R^1M^1\text{-}O\text{-}M^2R^2_2Cp \qquad (I),$$

comprising reacting a complex of the general formula (II)

$$CpM^1R^1(OH) \qquad (II)$$

with a complex of the general formula (III)

$$CpM^2R^2_3, \qquad (III),$$

wherein Cp, $R^1$, $R^2$, $M^1$ and $M^2$ are as defined above, under conditions sufficient to cause polymerization of the at least one monomer.

In another aspect, this document features a complex of the general formula (II)

$$CpM^1R^1(OH) \qquad (II)$$

wherein

Cp independently is a cyclopentadienyl, indenyl or fluorenyl ligand that can be substituted, or a ligand isolobal to cyclopentadienyl, $M^1$ is Zr, Ti or Hf, and $R^1$ is a halide, linear or branched or cyclic alkyl, aryl, amido, phosphido, alkoxy or aryloxy group that can be substituted.

In still another aspect, this document features a bimetallic catalyst comprising (a) the oxygen-bridged bimetallic complex of the general formula (I) as defined above, and (b) an activator selected from an alumoxane, trialkylaluminum, or a fluoro-organoborate compound or a mixture of two or more of these. The activator can be methylalumoxane (MAO) or trialkylaluminum.

This document also features a polymerization process comprising contacting at least one monomer with the bimetallic catalyst described above under polymerization conditions. The monomer can comprise at least one $C_{2\text{-}6}$-alkene. The monomer can comprise carbon dioxide.

In still another aspect, this document features a polyethylene (LLDPE) with a content of 0.5 to 3% of branches as determined by $^{13}C$ NMR, which is obtainable by a process described herein.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Synthesis of Cp*$_2$ZrMe(OH) (1)

The controlled hydrolysis of Cp*$_2$ZrMe$_2$ with one equivalent of water in n-hexane at $-30°$ C. to room temperature ($23°$ C.) resulted in the formation of Cp*$_2$ZrMe(OH) (1) in high yield with the elimination of methane.

Compound 1 is the first zirconium compound which is bonded to a methyl and OH group at the same zirconium atom. 1 is monomeric in the solid state and the Me and OH groups are not involved in hydrogen bonding as shown by X-ray structural analysis and IR spectroscopy. Compound 1 is stable and does not eliminate methane even at elevated temperatures to form an oxo-bridged complex unlike Cp*$_2$ZrH$_2$, which gives an oxo-bridged complex under elimination of H$_2$ when treated with water in a 2:1 stoichiometry. While not being bound to any theory, this may be due to the fact that the zirconium center is surrounded by sterically bulky Cp* ligands, which avoid complex 1 from dimerizing with loss of water.

Compound 1 is soluble in hexane, toluene, ether, THF, and dichloromethane. It was characterized by EI mass spectrometry, elemental analysis, $^1H$ and $^{13}C$ NMR, and IR spectroscopy. The $^1H$ NMR spectrum of 1 reveals a singlet for CH$_3$ protons (−0.2 ppm), which appears at low field as compared with the CH$_3$ protons (−0.62 ppm) of Cp*$_2$ZrMe$_2$. This can be explained by considering the electron withdrawing nature of the oxygen in the OH group attached to the Zr center. A single resonance (1.8 ppm) is observed for the methyl protons of the Cp* rings. The presence of the hydroxyl group is confirmed by a resonance of the OH proton (4.2 ppm) and an O—H stretching mode (3680 cm$^{-1}$) in the IR spectrum. The MS spectrum of compound 1 is interesting when compared with that of Cp*$_2$Zr(OH)$_2$, which gives an intense peak at m/z 376 ($^{90}$Zr) corresponding to the oxozirconium cation [Cp*$_2$ZrO]$^+$, whereas compound 1 shows an intense peak at m/z 377 ($^{90}$Zr) corresponding to [M$^+$-Me]. This indicates the low acidic character of the proton attached to oxygen, which may be due to the strong electron donating nature of the methyl groups.

Molecular Structure of 1

Figure 1:
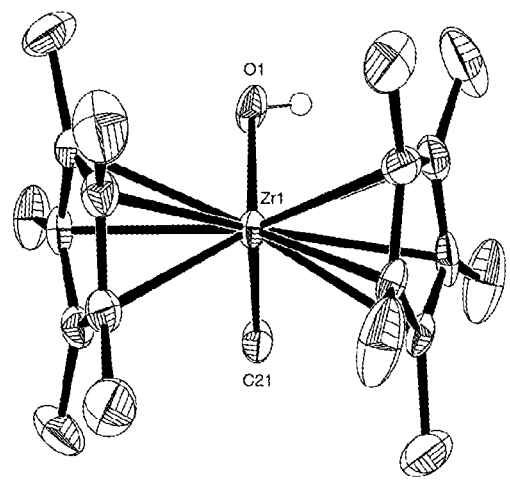
FIG. 1 is a drawing of the molecular structure of 1. Thermal ellipsoids set at 50% probability level. H atoms, except for the OH group, are omitted for clarity.

Crystals of 1 suitable for X-ray structural analysis were obtained from n-hexane at −20° C. Compound 1 crystallizes in the orthorhombic space group $P2_12_12_1$. The Zr center is bound to two Cp* groups and to two ancillary ligands (Me and OH) adopting a distorted tetrahedral geometry around the metal (FIG. 1). The OH and methyl positions and also one Cp* ring are disordered. The O(1)-Zr(1)-C(21) bond angle (95.5(2)°) and the angle involving the centroids of the Cp* rings (137.6°) are comparable to those of the corresponding $Cp*_2Zr(OH)_2$ (O—Zr—O, av 98.9(2)° and Cp* angle av 137.7(5)°) suggesting a steric interaction between the methyl-methyl groups of the Cp* ligands.

Theoretical Study on Compound 1

To further investigate the bonding situation around the zirconium atom and the unusual stability of compound 1 compared to $Cp*_2ZrH(OH)$ which could not be isolated, a NBO analysis including donor and acceptor interactions has been performed for the molecules. This analysis shows that the compounds vary significantly in the charge on the central atom. For compound 1 the charge is 1.82, and for $Cp*_2ZrH(OH)$, it is 1.58. For compound 1 with a Zr—C bond which can best be described as polar covalent. The small charge value of 1.58 for compound $Cp*_2ZrH(OH)$ may be the result of the hydrogen atom which carries a small negative charge of −0.30 thus leading to a hydridic character.

The weak acid-strength of these compounds can be put into an order by taking into account the two electron stabilization interactions of the O—H bond with other molecular orbitals which can be described as a donor acceptor interaction. Summing up all the contributions the ordering is 1 (33.3 kcal/mol)>$Cp*_2ZrH(OH)$ (29.6 kcal/mol) with 1 being the weakest acid. As a consequence, the stability of complex 1 can be attributed to the weak acidic character of the proton in OH and steric bulkiness of the Cp* ligands.

Synthesis of $Cp*_2MeZr$—O—$TiMe_2Cp*$ (2)

The unusual kinetic stability of 1 allows its further reaction with $Cp*TiMe_3$ in ether at −30° C. to room temperature (23° C.) under elimination of methane to form the heterobimetallic compound (2) containing Zr—O—Ti moiety in good yield. When a solution of $Cp*TiMe_3$ in ether was added drop by drop to the solution of 1 in ether (−30° C.) a precipitate was formed. After stirring at room temperature for 12 h the solvent was removed in vacuum and the crude product was washed with n-hexane.

Compound 2 is insoluble in n-hexane, pentane, and toluene, but sparingly soluble in diethyl ether and THF at room temperature, whereas soluble in hot toluene. Complex 2 was characterized by $^1H$ and $^{13}C$ NMR spectroscopy, EI mass spectrometry, and elemental analysis. The $^1H$ NMR spectrum of 2 shows two singlets (0.22 and 0.4 ppm) which can be assigned to the Me protons of $TiMe_2$ and ZrMe respectively, whereas the methyl protons on Cp* of Zr and Ti resonate as two different singlets (1.8 and 2.2 ppm) respectively. The EI mass spectrum ($^{90}Zr$) exhibits an intense peak at m/z 574 $[M-2Me]^+$, and the peak at m/z 589 (6%) was assigned to $[M-Me]^+$.

Molecular Structure Description of 2

Figure 2:
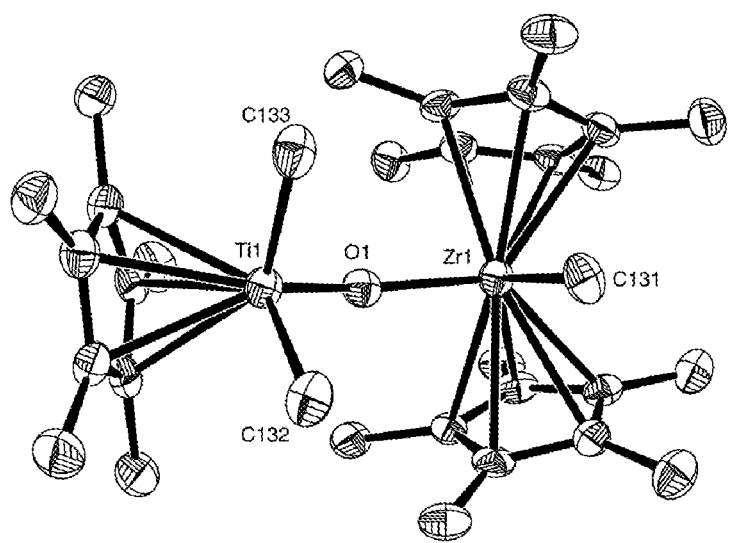
FIG. 2 is a drawing of the molecular structure of 2. Thermal ellipsoids set at 50% probability level. H atoms, except for the OH group, are omitted for clarity.

Suitable crystals for X-ray structural analysis were obtained by cooling the hot toluene solution of 2. Complex 2 crystallizes as a non-merohedral twin in the monoclinic space group Pc with two nearly identical molecules in the asymmetric unit. The molecular structure is shown in FIG. 2.

Compound 2 exhibits a bent Zr—O—Ti core. The Zr and Ti show highly distorted tetrahedral geometry. The coordination sphere of the Zr center consists of two Cp* ligands, one Me group, and one (μ-O) unit, while that of the Ti has Cp* ligand, two Me groups, and one (μ-O) unit. The Me groups on Ti and Zr are in staggered conformation. The Zr—C(131) bond distance (2.295(6)Å) is comparable to the average Zr—C bond length in the complex $Cp_2Zr$—$[CH_2SiMe_3]_2$[10] (av 2.284 Å) but is longer than the (av 2.251 Å) value found with $(\eta^5-C_9H_7)_2ZrMe_2$.[10] The Zr(1)-O(1)-Ti(1) bond angle (av 155.9) is significantly narrower when compared with the homobimetallic angles M-O-M (M=Zr, Ti) in compounds $(Cp_2ZrMe)_2(\mu-O)(174.1(3)°)$ and $[Cp_2Ti(CF_3C=C(H)CF_3)]_2(\mu-O))(170.0(2)°)$. The angle between the centroids of Cp* and the Zr center (134.1°) is also smaller when compared with that of compound 1 (137.6°) and the zirconium dihydroxide (137.7(5)°). But these angles are much wider than those of highly sterically congested alkoxide bridged clusters $(Ti_4Zr_2O_4(OBu)_n(OMc)_{10}$ (OMc=methacrylate, n=2,4,6) (98.8(2)° to 108.61(8)°)). The Zr(1)-O(1) (2.022(4)Å) bond distance is slightly longer when compared with the corresponding oxygen-bridged (μ-O) compounds $(Cp_2ZrL_2)_2(\mu-O)$ (L=Me, $SC_6H_5$) (1.945(1) and 1.966(5)Å) but shorter than those of heterobimetallic alkoxide bridged clusters $((Ti_4Zr_2O_4(OBu)_n(OMc)_{10}$ (n=2,4,6) Zr—O, av 2.189(2)Å). The Ti(1)-O(1) (1.816(4)Å) bond distance is slightly shorter than those in the μ-O compound $[Cp_2Ti(CF_3C=C(H)CF_3)]_2$ (μ-O) (av Ti—O, 1.856(6)Å) and alkoxide bridged cluster $((Ti_4Zr_2O_4(OBu)_n(OMc)_{10}$ (n=2,4,6), Ti—O, av 2.041(5)Å).

The oxygen-bridged bimetallic complex of the general formula (I) can be employed in a bimetallic catalyst which is especially useful for polymerization processes, specifically olefin polymerization processes.

A bimetallic catalyst can comprise (a) the oxygen-bridged bimetallic complex of the general formula (I) as defined herein, and (b) an activator selected from an aluminoxane, trialkylaluminum, or a fluoro-organoborate compound, or a mixture of two or more of these.

The aluminoxane can be an $C_{1-6}$-alkyl alumoxane, (e.g., methyl alumoxane (MAO)). The activation of the oxygen-bridged bimetallic complex may be performed as disclosed in, for example, WO 01/83498. Trialkylaluminum can be $AlR_3$ with R independently $C_{1-12}$-alkyl, such as $C_{1-3}$-alkyl. $Al(CH_3)_3$ can be particularly useful.

The catalyst can be free of MAO and only contain the trialkyl-aluminum as an activator.

The bimetallic catalyst can be employed in a polymerization process comprising contacting at least one monomer with a bimetallic catalyst as defined above under polymerization conditions.

The monomer can comprise at least one $C_{2-6}$-alkene, for example ethylene, propylene, butene, pentene, or hexene. The monomer may further comprise carbon dioxide ($CO_2$) which can be incorporated in the polymer backbone to give a biodegradable polymer, specifically in the case $M^2=Zn$.

Respective olefin polymerisation processes are also disclosed in WO 01/83498, WO 2004/060864, WO 2005/044866, WO 2005/090373 and WO 2006/065001 which are herein incorporated by reference in their entirety.

The polyethylene (LLDPE) obtained can have a content of 0.5 to 3% of branches, e.g., 0.5 to 1%, 1 to 2.5% or 2.5 to 3%, as determined by $^{13}C$ NMR.

TABLE 1

Crystal Data and Structure Refinement for Compounds 1 and 2

| | 1 | 2 |
|---|---|---|
| formula | $C_{21}H_{34}OZr$ | $C_{33}H_{54}OTiZr$ |
| formula weight | 393.7 | 605.88 |
| color | colorless | Yellow |
| crystal system | orthorhombic | monoclinic |
| space group | $P2_12_12_1$ | Pc |
| a, Å | 8.035(2) | 8.601(2) |
| b, Å | 10.948(3) | 15.399(2) |
| c, Å | 22.256(3) | 23.084(3) |
| α, deg | 90 | 90.0 |
| β, deg | 90 | 94.41(2)° |
| γ, deg | 90 | 90.0 |
| V, Å$^3$ | 1958(1) | 3048.3(9) |
| Z | 4 | 4 |
| $\rho_{calc}$, Mg m$^{-3}$ | 1.336 | 1.320 |
| μ, mm$^{-1}$ | 0.565 | 5.184 |
| F (000) | 832 | 1288 |
| θ range for data collection, deg | 1.83 to 26.39 | 2.87 to 59.42 |
| index ranges | $-10 \leq h \leq 10$ | $-9 \leq h \leq 9$ |
| | $0 \leq k \leq 13$ | $-16 \leq k \leq 17$ |
| | $0 \leq l \leq 27$ | $-25 \leq l \leq 25$ |
| no. of reflections collected | 36648 | 52720 |
| no. of independent reflections ($R_{int}$) | 4003 | 11233 |
| refinement method | Full-matrix least-squares on $F^2$ | Full-matrix least-squares on $F^2$ |
| R1, wR2$^b$ (all data) | 0.0250, 0.0625 | 0.0496, 0.1325 |
| largest diff peak, hole (e Å$^{-3}$) | −0.433/+0.782 | −0.799/+0.551 |

TABLE 2

Selected Bond Distances (Å) and Angles (deg) for Compounds 1 and 2

| Compound 1 | | | |
|---|---|---|---|
| Zr(1)—O(1) | 2.040(4) | O(1)—Zr(1)—C(21) | 95.5(2) |
| Zr(1)—C(21) | 2.302(7) | $X_{Cp}*_1$—Zr—$X_{Cp}*_2$ | 137.6 |
| Compound 2 | | | |
| Zr(1)—O(1) | 2.022(4) | Zr(1)—O(1)—Ti(1) | 156.1(2) |
| Ti(1)—O(1) | 1.816(4) | $X_{Cp}*_1$—Zr(1)—$X_{Cp}*_2$ | 134.1 |
| Zr(1)—$X_{Cp}*_1$ | 2.289 | O(1)—Zr(1)—C(131) | 94.8(2) |
| Zr(1)—$X_{Cp}*_2$ | 2.269 | O(1)—Ti(1)—C(132) | 106.3(2) |
| Ti(1)—$X_{Cp}*$ | 2.092 | O(1)—Ti(1)—C(133) | 105.3(2) |
| Zr(1)—C(131) | 2.295(6) | | |
| Ti(1)—C(132) | 2.120(6) | | |
| Ti(1)—C(133) | 2.123(6) | | |

$X_{Cp}$ = Centroid of the Cp ring

Computational Results

Theoretical Study Results on Complex 1

TABLE 3

Important Geometry Parameters for Complex 1 (Cp*$_2$ZrMe(OH))

| | [A, Å°] |
|---|---|
| Zr—CH3 | 2.29859 |
| Zr—OH | 2.02099 |
| O—H | 0.96156 |
| angle C—Zr—O | 93.92 |
| angle H—O—Zr | 123.98 |
| angle cp*-Zr-cp* | 136.96 |
| dihedral angle C—Zr—O—H | 80.47409 |

TABLE 4

Important Geometry Parameters for the Hydride Analogue of Complex 1 (Cp*$_2$ZrH(OH))

| | [A, Å°] |
|---|---|
| Zr—H | 1.84655 |
| Zr—OH | 2.01837 |
| O—H | 0.96122 |
| angle H—Zr—O | 97.87 |
| angle H—O—Zr | 125.58 |
| angle cp*-Zr-cp* | 134.32 |
| dihedral angle H—Zr—O—H | 83.57 |

Polymerization of Ethylene by Cp*$_2$MeZr—O—TiMe$_2$Cp* (2): A Comparison with (1:1) Mixtures of Cp*$_2$ZrMe$_2$ and Cp*TiMe$_3$ (A)

Figure 3:
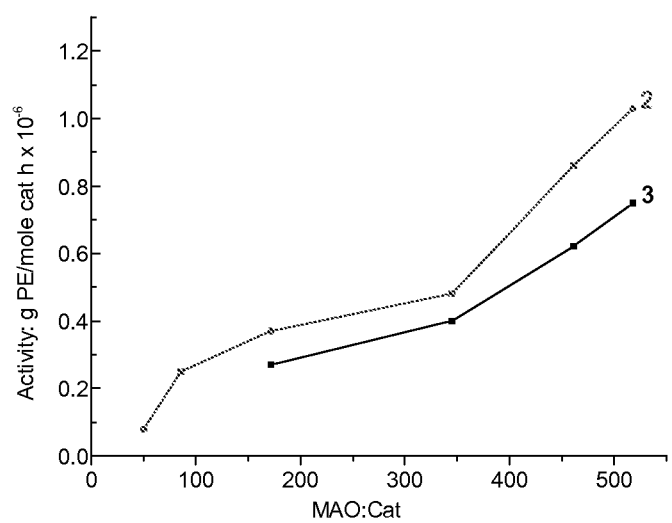
FIG. 3 is a plot showing activity against MAO to catalyst ratios of 2 and A (3).

Compound 2 catalyzes the polymerization of ethylene in toluene when activated with MAO. All polymeric materials were isolated as white powders. To compare the catalytic activity of 2 with that of (1:1 mixtures of Cp*$_2$ZrMe$_2$ and Cp*TiMe$_3$) A, polymerization of ethylene using MAO/A as a catalyst was performed under conditions similar to those used for MAO/2. Table 5 summarizes the activity of catalysts 2 and A. The activity of 2 is higher compared to that of A under the same condition. Table 5 represents the results of ethylene polymerization data. FIG. 3 shows the comparison of the activities of 2 and A. Compound 2 exhibits good activity even at low MAO/2 ratio. The polymerization data exhibits that the complex 2 is very active even at low (86:1) MAO to catalyst ratio in comparison to A, which under the same condition gives trace amount of polyethylene which could not be recorded. This high activity in 2 may be due to the bridging oxygen which enhances the Lewis acidity at the metal centers.

TABLE 5

Ethylene polymerization data for 2 and A[a]

| catalyst | MAO:catalyst | t (min) | T (° C.) | PE (g) | a (×10⁶) | $M_w \times 10^{-3}$ | $M_w/M_n$ | $T_m$[b] (° C.) |
|---|---|---|---|---|---|---|---|---|
| 2 | 86 | 20 | 25 | 2.7 | 0.25 | 17.45 | 4.17 | 134.1 |
| 2 | 172 | 20 | 25 | 4.1 | 0.37 | 18.84 | 7.99 | 125.9 |
| 2 | 345 | 20 | 25 | 5.3 | 0.48 | 36.18 | 11.65 | 124.5 |
| 2 | 461 | 20 | 25 | 9.5 | 0.86 | 32.35 | 13.10 | 139.1 |
| 2 | 518 | 20 | 25 | 10.4 | 0.95 | 21.19 | 5.68 | 122.2 |
| 2[c] | 172 | 10 | 83 | 1.5 | 0.69 | | | |
| A | 172 | 20 | 25 | 3.1 | 0.27 | | | |
| A | 345 | 20 | 25 | 4.7 | 0.40 | | | 118.3 |
| A | 461 | 20 | 25 | 7.2 | 0.62 | | | 116.4 |
| A | 518 | 20 | 25 | 8.7 | 0.75 | | | 120.0 |

[a]polymerization condition; 2 = 33 μmol, A = 35.3 μmol, 100 mL of toluene at 25° C., at 1 atm ethylene pressure. Activity (a) = g PE/mol cat · h.
[b]DSC.
[c]polymerization condition; 2 = 13.2 μmol, 83° C., at 1 atm ethylene pressure.

Thermal Stability

For efficient catalytic processes, the ideal situation is that the catalyst has to be both highly active and thermally stable. Good stability of the complex at high temperature is one crucial factor for the application of metallocene complexes on an industrial scale for olefin polymerization. To investigate the thermal stability of complex 2, polymerization was carried out at high temperature (83° C.). The complex exhibits good thermal stability and shows an increase in activity by almost two times of that at room temperature (see Table 3). One reasonable explanation is the high oxophilicity of Zr and Ti which forms strong metal-oxygen bonds and keeps the molecule intact. Furthermore, the sterically bulky and electron donating Cp* ligands stabilize the cation formed during the catalytic process. The mixture of A becomes dark above 50° C. indicating the decomposition of Cp*TiMe₃ which is sensitive to temperature. This document further relates to a polyethylene (LLDPE) with a content of 0.5 to 3% of branches (as determined by ¹³C NMR), obtainable by the process as defined above. Employing the catalyst in the polymerization of ethylene leads to very specific polyethylene having a defined degree of branching. The specific polymer properties achieved according to one embodiment are listed below.

Polymer Properties

DSC measurements show that the melting points ($T_m$) of the polyethylene produced by 2 are in the range of 122 to 139° C., which is in the typical range for LLDPE. The GPC measurements are monomodal for all polyethylene samples, except that for the reaction with the highest MAO to catalyst ratio (MAO/2=518) which exhibits bimodal.

The ¹³C NMR data confirm the branches (≤C₆ in length) along with the chain backbone for polymers produced by the complex 2. These polymer samples contain up to approximately 3% of branches (by ¹³C NMR, see supporting information). In contrast to these results, a 1:1 mixture of mononuclear Cp*₂ZrMe₂ and Cp*TiMe₃ as catalysts produces polymeric products with negligible branching, which is below the ¹³C detection limit. The greater branching in polyethylene produced by 2 probably reflects the increased metal-metal cooperative and ion-pair effects on the relative rates of propagation, chain transfer and comonomer enchainment. This may also indicate that the covalently linking heterobimetallic sites in complex 2 confine the Zr and Ti catalytic sites in such a way that a significant increase in the efficiency of the intramolecular oligomer incorporation/enchainment,[4] is occurring as suggested in FIG. 4.

Investigation of the Catalytic Species

An attempt was made to monitor the catalytic species formed during the activation of 2 with MAO by ¹H NMR spectroscopy at room temperature. The investigation of the ¹H NMR (MAO/2=10) exhibits the downfield shift for the Ti-Me (from 0.22 to 0.45 ppm), and it is accompanied by concomitant broadening of the Ti-Me signal. The initial 2:1 relative intensity of Ti-Me protons when compared with that of Zr-Me protons in 2 is reduced to 1:1 after the addition of MAO. This clearly suggests that one of the methyl groups attached to the Ti center interacts with the Al of MAO probably by forming a monocationic bridged complex [Cp*₂Zr(Me)OTi(Me)Cp*(μ-Me)AlMe₂]⁺[Me-MAO]⁻. The resonance for the bridged methyl is observed at −0.3 ppm. The methyl of the AlMe₃-MAO resonates at −0.73 ppm. The resonances for methyl protons of Cp* rings remain unchanged. The Zr-Me resonance remains unaffected with a slight downfield shift (0.4 to 0.5 ppm) indicating that the Zr-Me does not interact with Al of MAO at such a low concentration of MAO. However, gradual increase of MAO with 2 (MAO/2=20) results in broad resonances for the Zr-Me and Ti-Me groups indicating the involvement of Zr to form a dicationic heterobimetallic framework. The dicationic framework (FIG. 4) formed during the catalytic process is stabilized by the bulky and electron donating Cp* ligands.

Results of Computational Studies on Complex 2

It is evident from the crystal structure data that the M-O (M=Zr, Ti) bond length is short. Polymerization data shows that the compound exhibits high activity in ethylene polymerization. Without being bound to any theory, this may be due to the bridging oxygen, which causes short Zr—O and Ti—O bonds, indicative for high electron density within these bonds. As a consequence the electron density at the active metal sites is decreasing exhibiting enhanced Lewis acidic character. To support our findings from the experimental data, ab initio calculations were carried out aiming at the determination of the electronic density between Zr—O and Ti—O bonds.

As shown in Table 6, the resulting structure compares very well with the data obtained by X-ray diffraction, thus giving a solid foundation for the following bond analysis to describe the bonding situation quite well.

TABLE 6

Selected Calculated and X-ray Bond
Distances (Å) and Bond Angles (deg)

| Bond length | Calcd | X-ray | Bond angles | Calcd | X-ray |
|---|---|---|---|---|---|
| Zr(1)—O(1) | 2.039 | 2.022 | Zr(1)—O(1)—Ti(1) | 157.37 | 156.90 |
| Ti(1)—O(1) | 1.820 | 1.816 | O(1)—Zr(1)—C(131) | 94.89 | 94.80 |
| Zr(1)—C(131) | 2.289 | 2.295 | O(1)—Ti(1)—C(132) | 104.69 | 106.30 |
| Ti(1)—C(132) | 2.122 | 2.120 | O(1)—Ti(1)—C(133) | 104.74 | 105.3 |

Figure 4:
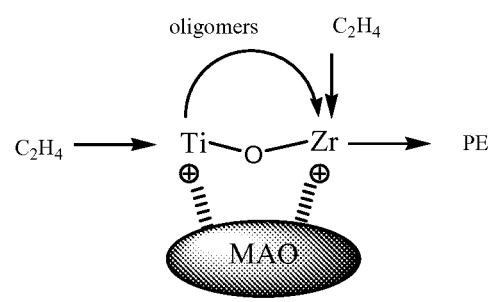
FIG. 4 is a depiction of a probable pathway of preferential binding of olefin fragments for subsequent enchainment. PE=polyethylene.

The NBO-analysis shows that the bonds formed between the metal atoms and the oxygen lead to a significant build-up of electron density on the oxygen atom. The distribution of electrons can be best described as locating 90% in a p-rich orbital of oxygen and leaving only 10% in a d-orbital of the metal. FIGS. 3 and 4 of the corresponding bonds show that electron density on the Zr atom is more depleted compared with that of the Ti atom.

This bonding scenario of 2 suggests that the Zr center is more Lewis acidic when compared with that of the Ti center. The NMR experiment reveals that the initial activation by MAO occurs at the titanium atom. This can be explained by the steric bulk of the Cp* ligands around the metal centers and the electronic stabilization of the corresponding cations. The steric bulk of Cp* ligands makes the Zr center kinetically less active towards the initial activation by MAO as compared with that of titanium, which has only one Cp* ligand in its coordination sphere. The high electron density on the titanium stabilizes its cation. It can be assumed that the Ti center initiates the polymerization and produces oligomers. Then the subsequent enchainment of oligomers by the Zr center occurs due to extreme proximity, and enhanced Lewis acidity as shown by the calculation (Scheme in FIG. 4; PE=polyethylene).

Complex 2 produces LLDPE with small but significant levels of $C_4$-$C_6$ alkyl branching. The bridging oxygen plays an important role in complex 2. First, it helps to form a kinetically and thermally stable Zr—O—Ti unit. Second, it can bring the two metallic centers to close proximity which helps to increase the cooperative effect between the metallic centers. Third, it enhances the Lewis acidity at the metallic centers and in turn leads to an increase in its catalytic activity.

The invention will be further described in the following examples, which do not limit the scope of the invention described in the claims.

EXAMPLES

General Comments

All experimental manipulations were carried out under an atmosphere of dry argon using standard Schlenk techniques. The samples for spectral measurements were prepared in a glovebox. The solvents were purified according to conventional procedures and were freshly distilled prior to use. $Cp*_2ZrCl_2$, $Cp*_2ZrMe_2$, and $Cp*TiMe_3$ were prepared by the procedures published by Manriquez et al. (1978) *J. Am. Chem. Soc.* 100:3078; Manriquez et al. (1978) *J. Am. Chem. Soc.* 100:2716; and Mena et al. (1989) *Organometallics* 8:476, respectively. $Cp*TiCl_3$ was purchased from Aldrich. NMR spectra were recorded on a Bruker Avance 500 instrument, and the chemical shifts are reported with reference to tetramethylsilane (TMS). $^{13}C$ NMR assays of polymer microstructure were conducted in 1,1,2,2-tetrachloroethane-$d_2$ at 90° C. Resonances were assigned according to the literature for polyethylene and ethylene+α-olefin copolymers.

IR spectra were recorded on a Bio-Rad Digilab FTS-7 spectrometer. Mass spectra were obtained on a Finnigan MAT 8230 spectrometer by the EI technique. Melting points were obtained in sealed capillaries on a Büchi B 540 instrument. Elemental analyses were performed at the Analytical Laboratory of the Institute of Inorganic Chemistry at Göttingen, Germany.

Example 1

Synthesis of $Cp*_2ZrMe(OH)$ (1)

$Cp*_2ZrMe_2$ (0.5 g, 1.28 mmol) was dissolved in n-hexane (30 mL). The resulting solution was cooled to −30° C. and 1 equivalent of $H_2O$ (23 μL) was added rapidly under vigorous stirring. The temperature of the solution was maintained at −30° C. for 10 min, then was slowly warmed to ambient temperature and stirred for another 30 min till methane evolution has ceased. The solvent was removed in vacuum to obtain colorless crystalline material. Yield 0.36 g (72%). Mp 202° C. (decomp). IR (KBr): $\tilde{v}$=3680, 2965, 2908, 1492, 1440, 1380, 1262, 1099, 1022, 941, 865, 801 $cm^{-1}$; $^1H$ NMR (500 MHz, $C_6D_6$, 25° C., TMS): δ: −0.2 (s, 3H, Zr—$CH_3$), 1.8 (s, 30H, $C_5(CH_3)_5$), 4.2 (s, 1H, OH); $^{13}C$ NMR (500 MHz, $C_7D_8$, 25° C., TMS): δ: 118.7 (s, $Cp*_2$, $C_{10}$), 27.0 (s, $CH_3$); MS (EI): m/z (%): 377 (100) [M-Me]$^+$; elemental analysis (%) calculated for $C_{21}H_{34}OZr$ (393.72): C, 64.06; H, 8.70. found: C, 63.86; H, 8.62.

Example 2

Synthesis of $Cp*_2MeZr$—O—$TiMe_2Cp*$ (2)

A solution of $Cp*TiMe_3$ (0.228 g, 1.00 mmol) in diethyl ether (30 mL) was added dropwise to a solution of 1 (0.394 g, 1.00 mmol) in diethyl ether (30 mL) at −30° C. The resulting solution was stirred at −30° C. for 5 min and was slowly warmed to ambient temperature. Vigorous methane elimination was noticed with concomitant formation of a precipitate. After stirring for additional 12 h the solvent was removed in vacuum and the crude product was washed with n-hexane, to give a yellow powder. Yield 0.5 g (64%). Mp 224° C. (decomp). $^1H$ NMR (500 MHz, $C_6D_6$, 25° C., TMS): δ: 0.22 (s, 6H, Ti—$(CH_3)_2$), 0.4 (s, 3H, Zr—$CH_3$), 1.8 (s, 30H, $C_5(CH_3)_5$), 2.2 (s, 15H, $C_5(CH_3)_5$); $^{13}C$ NMR (500 MHz, $C_7D_8$, 25° C., TMS): δ: 118.2 (s, $Cp*_2Zr$, $C_{10}$), 121.4 (s, $Cp*Ti$, $C_5$), 52.3 (s, Ti—$(CH_3)_2$), 34.8 (s, Zr—$CH_3$); MS (EI): m/z (%): 574.2 (100) [M-2Me]$^+$, 589.2 (6%) [M-Me]$^+$; elemental analysis (%) calculated for $C_{33}H_{54}OTiZr$ (605.88): C, 65.42; H, 8.98. found: C, 64.72; H, 8.92.

Example 3

X-Ray Structure Determination of 1 and 2

Data for the structure 2 were collected on a Bruker three-circle diffractometer equipped with a SMART 6000 CCD detector. The data for the structure 1 were collected on a STOE IPDS II diffractometer. Intensity measurements were performed on a rapidly cooled crystal. The structures were solved by direct methods (SHELXS-97) and refined with all data by full-matrix least squares on $FP^2$, see Sheldrick (1990) *Acta. Cryst.* A46:467; and Sheldrick (1997) M. SHELXS-97 and SHELXL-97. Program for Crystal Structure Refinement, Göttingen University, Göttingen, Germany, respectively. The hydrogen atoms on C—H bonds were placed in idealized positions and refined isotropically with a riding model, whereas the non hydrogen atoms were refined anisotropically. The OH and methyl positions and one of the Cp* rings in complex 1 are disordered. The data for 2 were collected on a non-merohedrally twinned crystal. The twin law is a 180° rotation about the reciprocal axis 012. They were refined with distance restraints and restraints for the anisotropic displacement parameters. Crystal data and selected bond lengths and angles are shown in Tables 1 and 2.

Example 4

Computational Details

The calculations were performed at the well established DFT level of theory making use of the B3LYP functional as implemented in the Gaussian program package employing a basis-set termed LanL2DZ for Zr and Ti and 6-31G for the remaining atoms. See, Lee et al. (1988) *Phys. Rev. B* 37:785; Miehlich et al. (1989) *Chem. Phys. Lett.* 157:200; Frisch et al. (2004) *Gaussian 03, Revision C*.02, Gaussian, Inc., Wallingford Conn., Hay and Wadt (1985) *J. Chem. Phys.* 82:270; Ditchfield et al. (1971) *J. Chem. Phys.* 54:724; Hariharan and Pople (1973) *Theo. Chim. Acta.* 28:213; and Rassolov et al. (2001) *J. Comp. Chem.* 22:976. In the first step the compound was fully optimized to its equilibrium structure. The analysis of the resulting electronic wavefunction for this structure was then used to obtain the electronic density at the atoms of interest. The analysis of the bonding situation was performed at the calculated equilibrium geometry by means of a NBO-analysis. See, Foster and Weinhold (1980) *J. Am. Chem. Soc.* 102:7211; Reed and Weinhold (1985) *J. Chem. Phys.* 83:1736; and Reed et al. (1988) *Chem. Rev.* 88:899.

Example 5

Ethylene Polymerization Experiments

Figure 5:
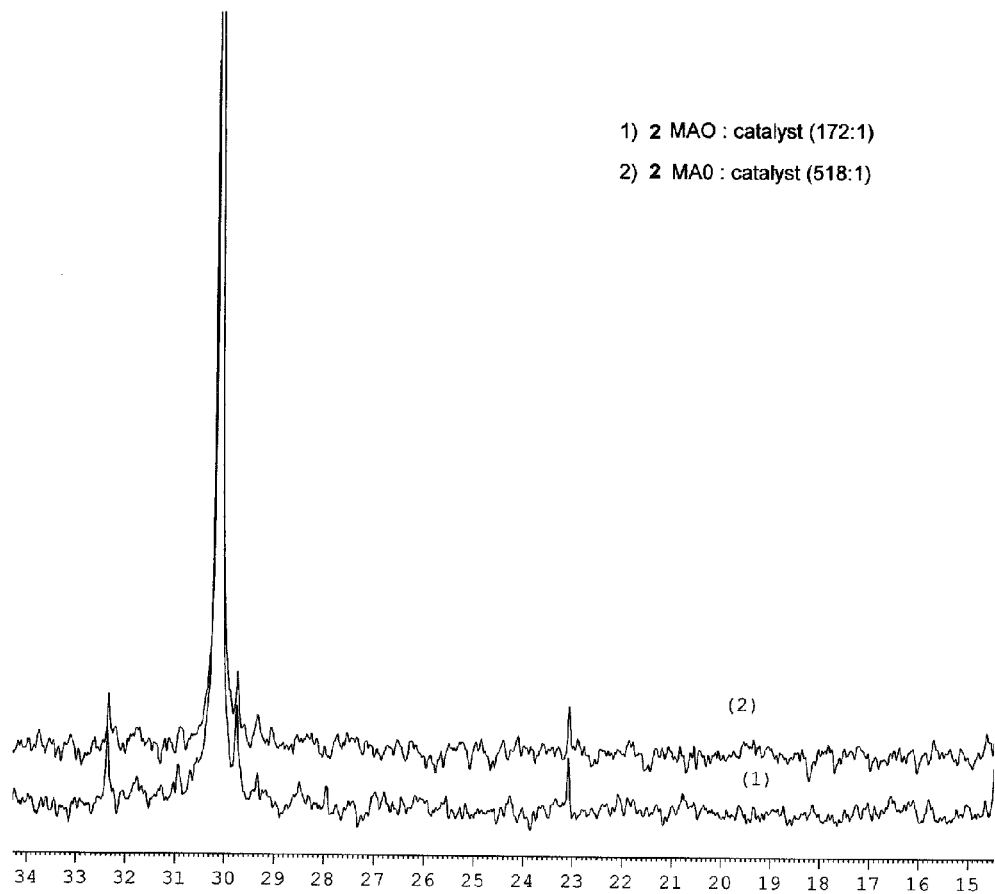
FIG. 5 is a $^{13}C$ NMR spectra of polyethylene samples produced by 2 revealing 3% branching (marked by *) 1) 2 MAO:catalyst (172:1), 2) 2 MAO:catalyst (518:1).
Figure 6:
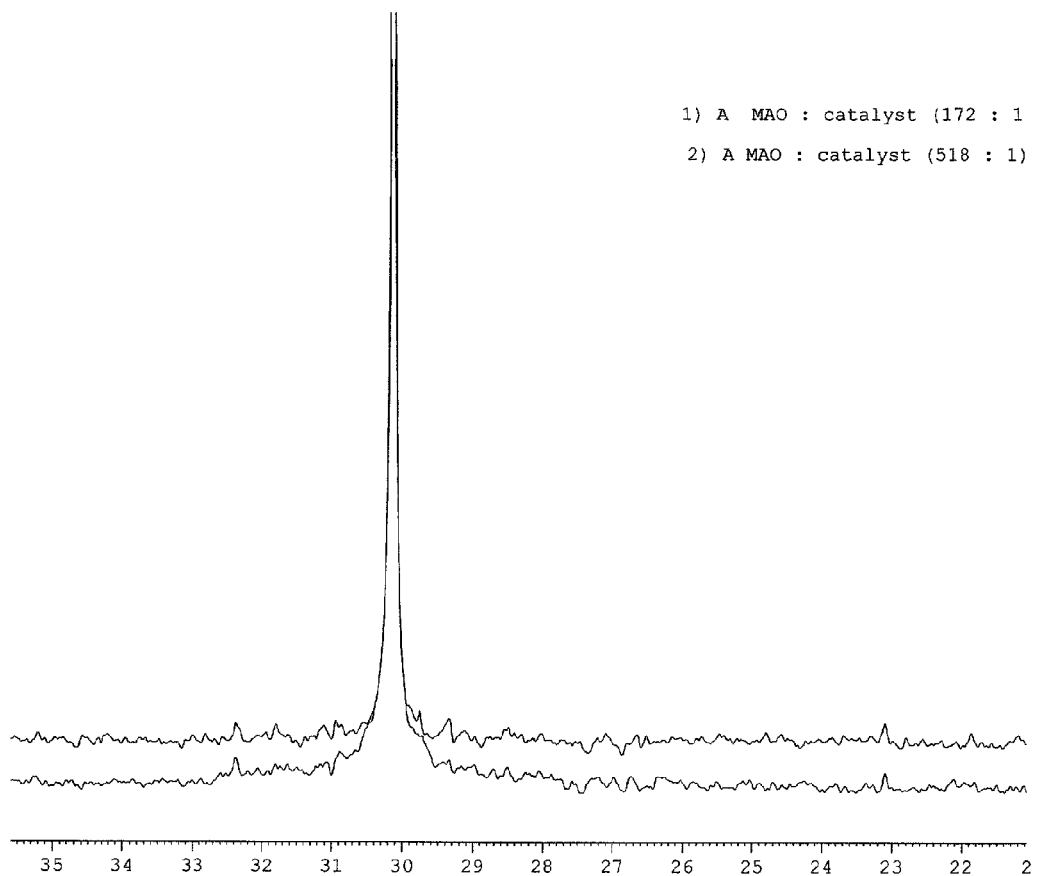
FIG. 6 is a $^{13}C$ NMR spectra of polyethylene samples produced by A with negligible branching 1) A MAO:catalyst (172:1), 2) A MAO:catalyst (518:1).

Ethylene polymerizations were carried out on a high vacuum line ($10^{-5}$ Torr) in an autoclave (Buchi). In a typical experiment, the catalyst (see Table 5) was taken and an appropriate amount of MAO (1.6 M, Aldrich) was added and stirred for 20 minutes for the activation. After stirring, the resulting mixture was placed into the autoclave using a gas tight syringe, which was previously filled with 100 mL of toluene under ethylene atmosphere (1 atm). After stirring for an appropriate time, the reaction was quenched using 15% acidified methanol and the white polyethylene formed was collected by filtration and dried. The results are shown in Table 5 and in FIGS. 5 and 6.

Example 6

Differential Scanning Calorimetry (DSC)

The polymer melting range was measured on a TA instrument 2920 (Modulated Differential Scanning Calorimeter) which was calibrated against indium metal. Typically ca. 4 mg samples were used (10° C./min).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A polymerization process comprising contacting at least one monomer with a bimetallic catalyst, the bimetallic catalyst comprising
    (a) the oxygen-bridged bimetallic complex of the general formula (I):

$$Cp_2R^1M^1\text{-O-}M^2R^2{}_2Cp \qquad (I)$$

wherein
    Cp is independently a cyclopentadienyl, indenyl or fluorenyl ligand that can be substituted,
    $R^1$, $R^2$ independently are halide, linear or branched or cyclic alkyl, aryl, amido, phosphido, alkoxy or aryloxy groups that can be substituted,
    $M^1$ is Zr, Ti or Hf, and
    $M^2$ is Ti or Zr; and,
    (b) an activator selected from an alumoxane, trialkylaluminum, or a fluoroorganoborate compound, or a mixture of two or more of these,
wherein the contacting is under conditions sufficient to cause polymerization of the at least one monomer.

2. The process of claim 1, wherein the monomer comprises at least one $C_{2-6}$-alkene.

3. The process of claim 1, wherein the monomer comprises carbon dioxide.

4. The process of claim 1, wherein Cp independently is a cyclopentadienyl ligand that can be substituted by 1 to 5 $C_{1-6}$-alkyl groups.

5. The process of claim 1, wherein $R^1$ and $R^2$ independently are $C_{1-6}$-alkyl groups.

6. The process of claim 1, wherein $M^1$ is Zr and $M^2$ is Ti.

7. The process of claim 1, wherein the activator is MAO or trialkylaluminum.

* * * * *

UNITED STATES PATENT AND TRADEMARK OFFICE
CERTIFICATE OF CORRECTION

PATENT NO.       : 8,598,284 B2
APPLICATION NO.  : 12/879088
DATED            : December 3, 2013
INVENTOR(S)      : Herbert W. Roesky and Prabhuodeyara M. Gurubasavaraj It is certified that error appears in the above-identified patent and that said Letters Patent is hereby corrected as shown below:

In the Claims:

Column 14, line 24, in Claim 1, delete "$Cp_2R^1M^1\text{-}O\text{-}M^2R^22Cp$" and insert -- $Cp_2R^1M^1\text{-}O\text{-}M^2R^2_2Cp$ --, therefor.

Signed and Sealed this
Twenty-second Day of April, 2014

Michelle K. Lee
*Deputy Director of the United States Patent and Trademark Office*